(12) United States Patent
Almansour et al.

(10) Patent No.: US 10,357,485 B1
(45) Date of Patent: Jul. 23, 2019

(54) ANTI-CANCER COMPOUND

(71) Applicant: KING SAUD UNIVERSITY, Riyadh (SA)

(72) Inventors: Abdulrahman Ibrahim Almansour, Riyadh (SA); Raju Suresh Kumar, Riyadh (SA); Natarajan Arumugam, Riyadh (SA); Kotresha Dupadahalli, Riyadh (SA); Jose Carlos Menendez, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/143,875

(22) Filed: Sep. 27, 2018

(51) Int. Cl.
*A61K 31/439* (2006.01)
*A61P 35/00* (2006.01)
*C07D 221/02* (2006.01)

(52) U.S. Cl.
CPC ............ *A61K 31/439* (2013.01); *A61P 35/00* (2018.01)

(58) Field of Classification Search
CPC .............................. A61K 31/439; A61P 35/00
See application file for complete search history.

(56) References Cited

U.S. PATENT DOCUMENTS

| | | | |
|---|---|---|---|
| 4,065,617 A | 12/1977 | Krapcho |
| 6,486,174 B2 | 11/2002 | Wang |
| 8,785,452 B2 | 7/2014 | Brodin |
| 8,859,625 B2 | 10/2014 | Suarez |
| 9,884,825 B2 | 2/2018 | Rawat |

OTHER PUBLICATIONS

Gali-Muhtasib, H., "Cell death mechanisms of plant-derived anti-cancer drugs: beyond apoptosis." Apoptosis 20.12 (2015): 1531-1562.*
Hewitson, T. D., "Renal tubulointerstitial fibrosis: common but never simple." American Journal of Physiology—Renal Physiology 296.6 (2009): F1239-F1244.*
Wielowieyska, S., "Psoriasis: course of disease and treatment." Advances in Dermatology & Allergology/Postepy Dermatologii i Alergologii 29.2 (2012): 118-122.*
Montserrat, E., "Treatment of chronic lymphocytic leukemia in advanced stages. A randomized trial comparing chlorambucil plus prednisone versus cyclophosphamide, vincristine, and prednisone." Cancer 56.10 (1985): 2369-2375.*
Kumar, R.S., et al., "A sustainable approach to the stereoselective synthesis of diazaheptacyclic cage systems based on a multicomponent strategy in an ionic liquid," Molecules. 2016, 21(2), 165.
Malathi et al., "Multicomponent [3+2] cycloaddition strategy: stereoselective synthesis of novel polycyclic cage-like systems and dispiro compounds," Tetrahedron Letters. 2015, 56(44), 6132-6135.
Arumugam et al., "A 1,3-dipolar cycloaddition-annulation protocol for the expedient region-, stereo- and product-selective construction of novel hybrid heterocycles comprising seven rings and seven contiguous stereocentres," Tetrahedron Letters. 2013, 54(20), 2515-2519.

* cited by examiner

*Primary Examiner* — John M Mauro
(74) *Attorney, Agent, or Firm* — Richard C. Litman

(57) ABSTRACT

An anti-cancer compound is a compound having the following structural formula:

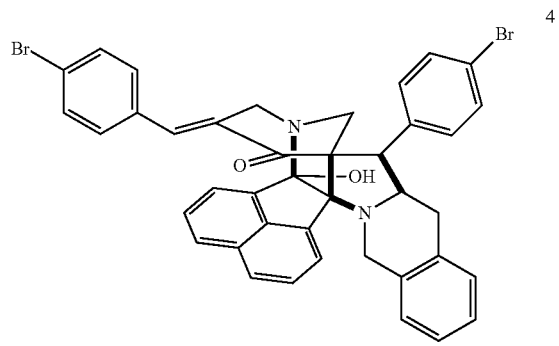

or a pharmaceutically acceptable salt thereof.

8 Claims, 15 Drawing Sheets

ANTI-CANCER COMPOUND

BACKGROUND

1. Field

The disclosure of the present patent application relates to heterocyclic compounds having biologically relevant activities, and particularly, to a polycyclic, cage-like, heterocyclic hybrid, anti-cancer compound and synthesis thereof.

2. Description of the Related Art

Cancers constitute a potentially lethal group of diseases characterized by unregulated proliferation and a deregulation of apoptotic mechanisms. Side effects associated with the use of current chemotherapeutic agents and the development of drug resistance are major obstacles to effective cancer treatment. Thus, identifying and developing new anti-cancer agents with improved efficacy and reduced side effects to complement the present chemotherapeutic strategies are perpetually needed. Development of novel anti-cancer agents with high selectivity and low toxicity remains an area of intensive research.

Apoptosis, programmed cell death in response to specific stimuli, is crucial for sustaining the physiologic balance between cell growth and cell death. Apoptosis can be triggered by two major pathways: an extrinsic pathway, which is triggered by binding of "death ligands" to "death receptors", and an intrinsic mitochondrial pathway, which is initiated by cytotoxicity. Both pathways are regulated by a group of proteases known as caspases. Targeting these pathways by chemotherapeutic drugs is a proven therapeutic strategy to control tumor growth and cancer progression.

Hybrid multifunctional molecules carrying more than one pharmacophoric entity, wherein each individual active entity exerts diverse modes of action, hold particular potential in the treatment of complex, multifactorial diseases, such as cancer. To this end, cage-like compounds provide an opportunity to join several active units in a single compact structure. For instance, gambogic acid, a naturally occurring cage-like compound, has been identified as a potent antitumor agent and has finished phase IIa clinical trials. The biological evaluation of gambogic acid derivatives indicates that the peripheral moieties are suitable sites for diverse modification, while the α,β-unsaturated moiety in the caged ring is essential for antitumor activity. Nevertheless, reports of anti-cancer studies of cage-like heterocycles comprising several pharmacophoric units in a single molecule are scarce.

Isoquinoline and pyrroloisoquinoline structural fragments are present in a large number of bioactive alkaloids that may hold anti-cancer properties. Piperidinone derivatives embedded with an α,β-unsaturated carbonyl group exhibit potent and promising activity against cancer cell lines. In particular, 3,5-bis(arylidene)-4-piperidones demonstrate $IC_{50}$ values in the low micromolar to submicromolar range toward a number of cell lines. Fluorescent properties of such piperidinone derivatives suggest their potential use as theranostic agents. Finally, some acenaphtho[1,2-b]pyrrole derivatives have shown submicromolar activity against certain cancer cell lines, motivating incorporation of such units in hybrid heterocyclic structures in order to study their pharmacological profile.

Multi-component reactions (MCR) are among the most efficient methods of accomplishing molecular complexity and diversity with a minimum number of synthetic steps. Therefore, the design of selective MCRs for green synthesis of diverse heterocycles having biological significance is a continuing challenge faced at the forefront of synthetic organic chemistry. Another class of transformations capable of generating several bonds in a single operation are [3+2] cycloadditions, which have been widely used to generate complex molecules from easily available starting materials in a single synthetic step. Ionic liquids are widely recognized as "green" solvents that serve as an alternative to the volatile organic solvents and are suitable for executing diverse organic reactions. The development of multicomponent reactions in ionic liquids is relatively unexplored.

Thus, a polycyclic cage-like heterocyclic hybrid useful as an anti-cancer agent solving the aforementioned problems is desired.

SUMMARY

An anti-cancer compound is a compound having the following structural formula:

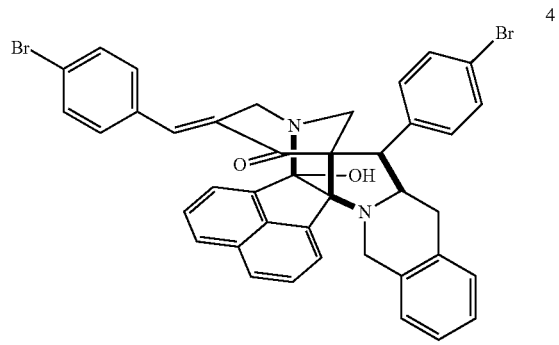

or a pharmaceutically acceptable salt thereof.

These and other features of the present disclosure will become readily apparent upon further review of the following specification and drawings.

BRIEF DESCRIPTION OF THE DRAWINGS

FIG. 7D is a graph depicting percentages of cells gated as follows: sub G0/G1, G0/G1, S, G2/M phase.

DETAILED DESCRIPTION OF THE PREFERRED EMBODIMENTS

An anti-cancer compound includes the following polycyclic, cage-like heterocyclic hybrid compound:

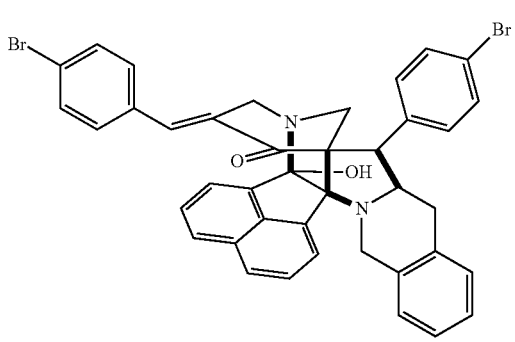

or a pharmaceutically acceptable salt thereof.

A pharmaceutically acceptable salt includes any non-toxic salt of the present compound, which is prepared by reacting a free acid with a suitable organic or inorganic base. Examples of such salts include, but are not limited to, acetate, benzenesulfonate, benzoate, bicarbonate, bisulfate, bitartrate, borate, bromide, calcium, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, potassium, salicylate, sodium, stearate, subacetate, succinate, tannate, tartrate, teoclate, tosylate, triethiodide, valerate.

Acids with which addition salts can be formed can include hydrohalic acids such as for example, hydrochloric acid and hydrobromic acid, and also phosphoric acid, nitric acid, monofunctional and bifunctional carboxylic acids, hydroxy carboxylic acids, such as, acetic acid, maleic acid, succinic acid, fumaric acid, tartaric acid, salicylic acid, sorbic acid and lactic acid, as well as sulphonic acids such as, p-toluenesulphonic acid and naphthaline-1,5-disulphonic acid.

The anti-cancer compound can be used as an active ingredient in a pharmaceutical composition for treating a proliferative disease, such as cancer. The cancer can include at least one of blood cancer, breast cancer, colon cancer, and lung cancer. The pharmaceutical composition can include the anti-cancer compound and a pharmaceutically acceptable carrier, diluent or excipient. A method for treating a proliferative disease, such as cancer, can include administering a therapeutically effective amount of the anti-cancer compound to a patient in need thereof. As would be understood by those skilled in the art of treating cancer, the terms "treat," "treating," or "treatment" do not necessarily mean that the cancer is completely cured, but encompass any inhibition of replication of cancer cells and/or reduction in the tumor size in the subject being treated. The anti-cancer compound can be administered by any conventional route of administration, including, but not limited to, intravenous, oral, subcutaneous, intramuscular, intradermal and parenteral.

Figure 1:
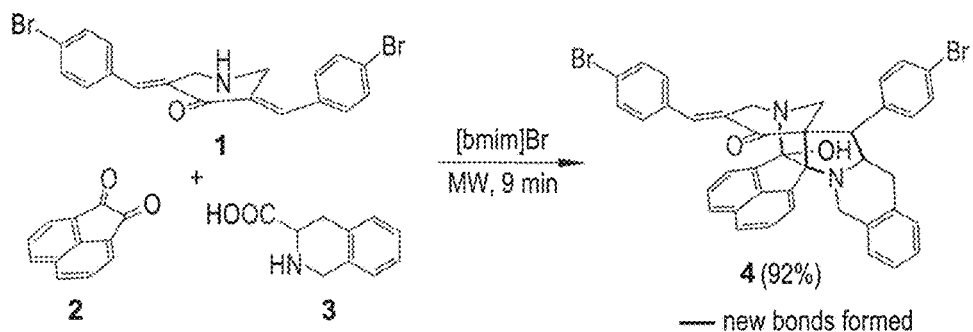
FIG. 1 shows an exemplary synthesis scheme for preparing polycyclic cage-like heterocyclic hybrid compound 4 according to an embodiment of the present subject matter
Figure 2:
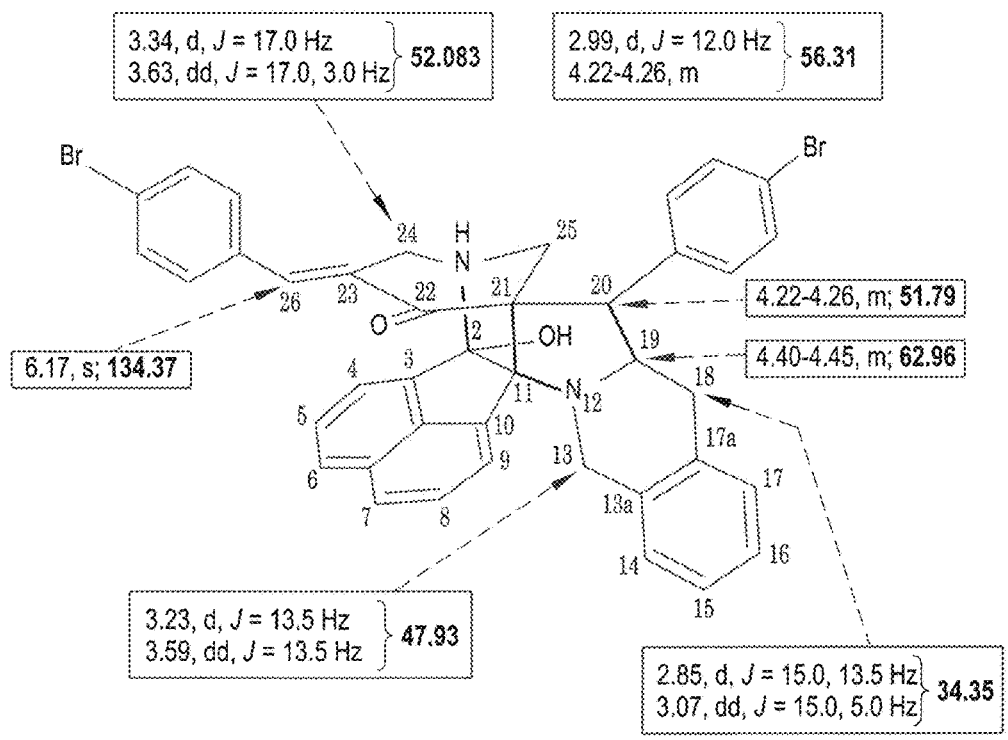
FIG. 2 illustrates selected $^1$H and $^{13}$C NMR chemical shifts of heterocyclic hybrid compound 4.

Stereoselective synthesis of compound 4 may be achieved by three-component domino reactions of 3,5-bis(E)-p-bromophenylmethylidene]tetrahydro-4(1H)-pyridinone (structure 1), acenaphthenequinone (structure 2) and 1,2,3,4-tetrahydroisoquinoline-3-carboxylic acid (structure 3) in ionic liquid, such as 1-butyl-3-methylimidazoliumbromide ([bmim]Br) under microwave conditions. An exemplary synthesis scheme for compound 4 is shown in FIG. 1. The three-component [3+2]-cycloaddition between the N-unsubstituted 3,5-bis[(E)-arylmethylidene]tetrahydro-4(1H)-pyridinone 1, acenaphthenequinone 2 and 1,2,3,4-tetrahydroisoquinoline-3-carboxylic acid 3 in [bmim]Br affords the polycyclic cage-like heterocyclic hybrid compound 4 at excellent yields (at least 92%). In a typical experimental protocol, as will be further described in the subsequent examples, an equimolar mixture of the starting materials 1, 2 and 3 in 100 mg of [bmim]Br was subjected to microwave irradiation at 100° C. for 9 min. After completion of the reaction, the resulting compound was isolated by extraction and further purified by column chromatography. The arbitrary atom numbering of compound 4 is shown in FIG. 2.

The structure of compound 4 was elucidated using Infrared (IR) and Nuclear Magnetic Resonance (NMR) spectroscopic studies. Selected $^1$H and $^{13}$C NMR chemical shifts of compound 4 are shown in FIG. 2.

Figure 3:
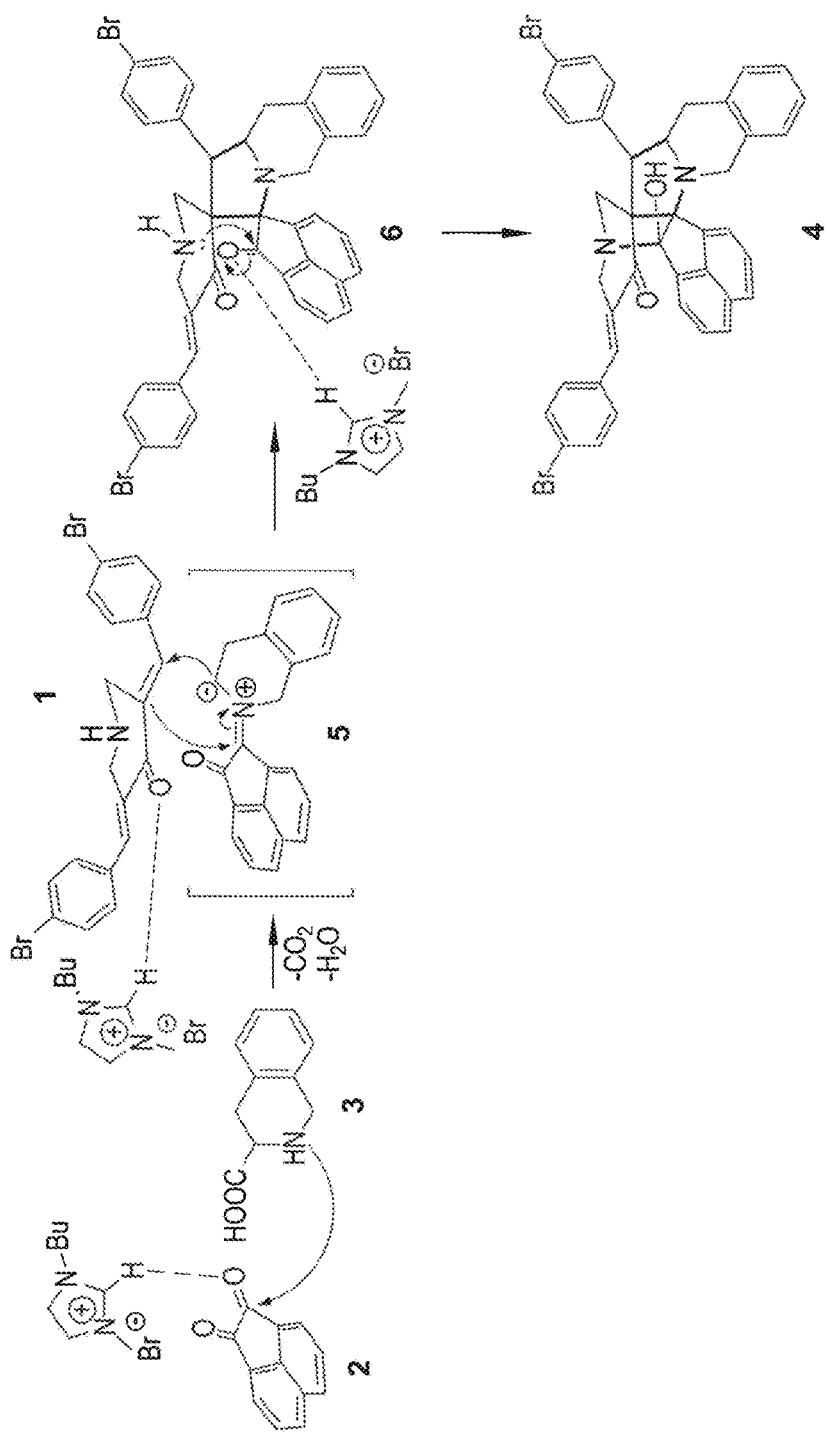
FIG. 3 illustrates a probable mechanism for the formation of polycyclic cage-like heterocyclic hybrid compound 4.

A plausible mechanistic proposal to account for the formation of compound 4 by the protocol disclosed herein is shown in FIG. 3. Initially, it is believed that the interaction of [bmim]Br with the carbonyl group of acenaphthenequinone 2 via hydrogen bonding increases the electrophilicity of the carbonyl carbon, facilitating the nucleophilic attack of the NH of 1,2,3,4-tetrahydroisoquinoline-3-carboxylic acid 3. Subsequent dehydration and concomitant decarboxylation would then furnish azomethineylide 5. The interaction of [bmim]Br with the carbonyl group of 3,5-bis[(E)-p-bromophenylmethylidene]tetrahydro-4(1H)-pyridinone 1 presumably activates the exocyclic double bond, allowing the initial addition reaction of the azomethineylide with the more electron deficient β-carbon of 1 to afford spiropyrroloisoquinoline 6. Subsequently, the interaction of [bmim]Br with the second carbonyl group of the acenaphthenequinone ring of spiropyrroloisoquinoline 6 presumably increases the electrophilicity of that carbonyl carbon, facilitating further annulation by the reaction of amino function of piperidone ring with the proximate carbonyl group resulting in the formation of the 4. One skilled in the art would understand this proposed mechanism to be nonlimitting of the process of synthesizing compound 4.

Figure 4:
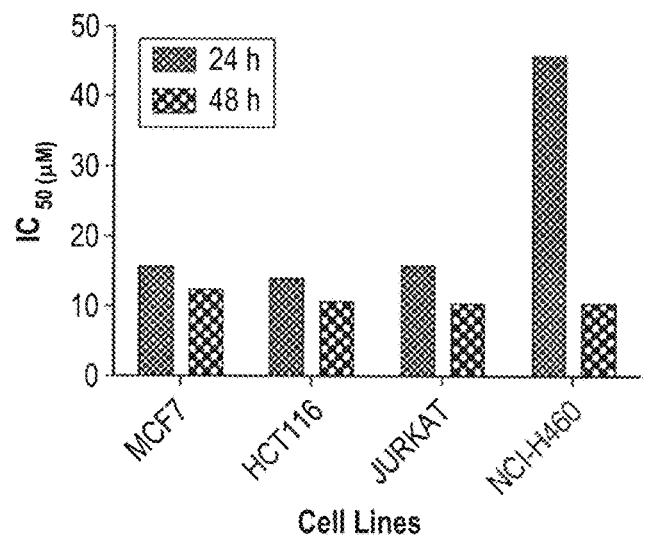
FIG. 4 is a graph showing cytotoxicity of heterocyclic hybrid compound 4 on different human cancer cells—MCF7, HCT116, Jurkat, NCI-H460—measured after 24 h and 48 h of treatment, determined by an MTT assay (mean $IC_{50}$ values are reported calculated from MTT assays performed in triplicate).
Figure 5:
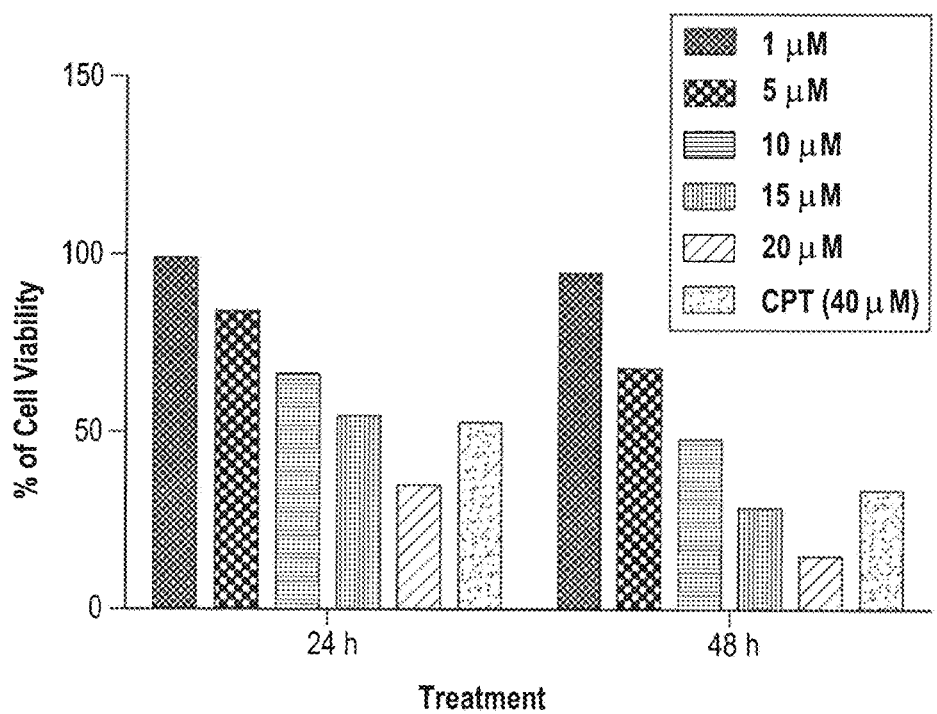
FIG. 5 is a graph showing antiproliferative effects of heterocyclic hybrid compound 4 (1-20 μM) on Jurkat cells after 24 h and 48 h of treatment (camptothecin (CPT 40 μM) is used as a positive control).
Figure 6A:
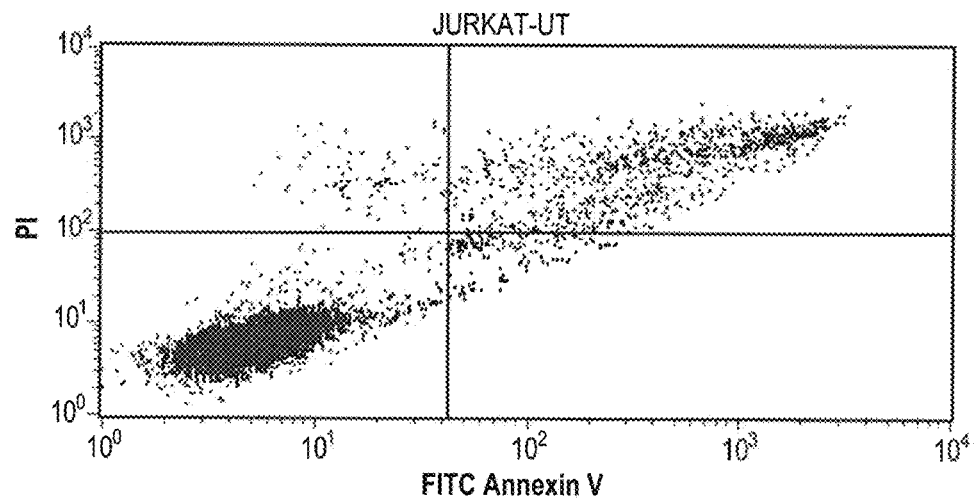
FIGS. 6A-6F show flow cytometric analysis of apoptosis in Jurkat cells: Annexin V-FITC/PI staining for untreated Jurkat cells (UT) (FIGS. 6A-6B), CPT treated Jurkat Cells (CPT; positive control) (FIGS. 6C-6D), and heterocyclic hybrid compound 4 treated Jurkat cells after 48 h of treatment (FIGS. 6E-6F).
Figure 6B:
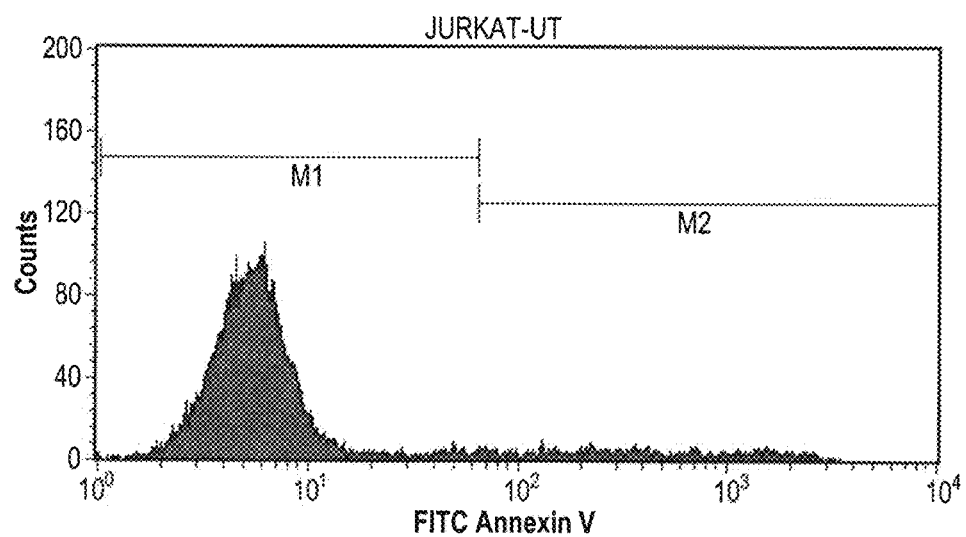
Figure 6C:
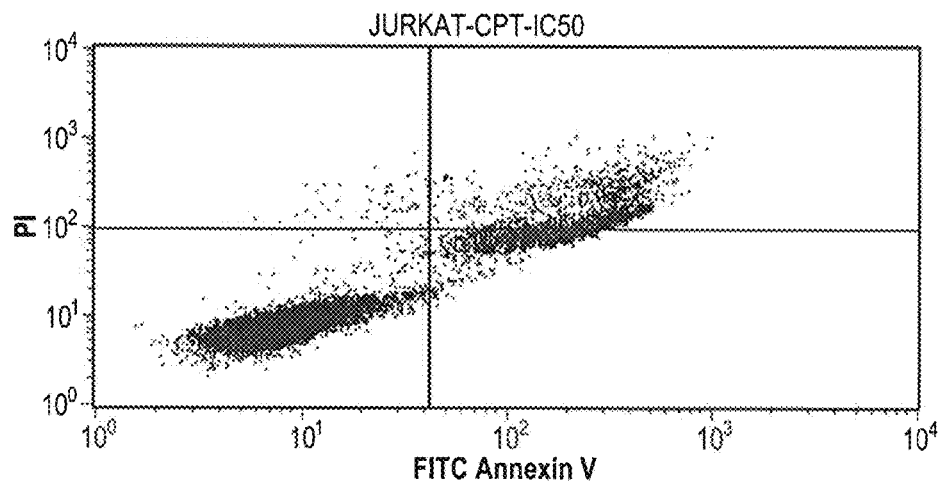
Figure 6D:
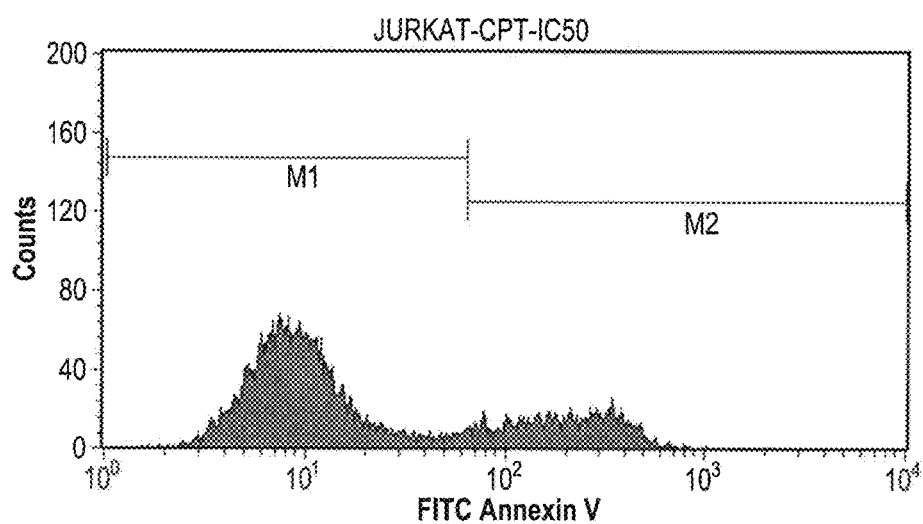
Figure 6E:
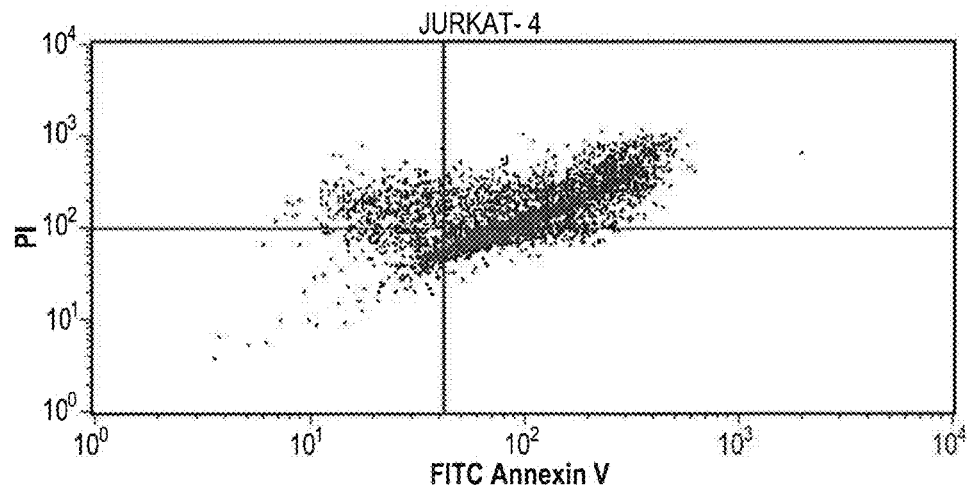
Figure 6F:
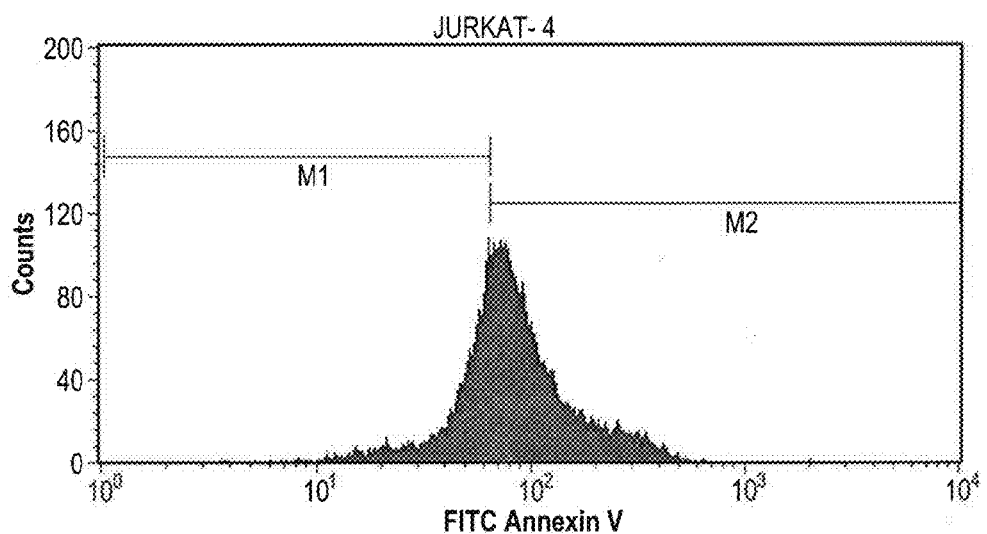
Figure 6G:
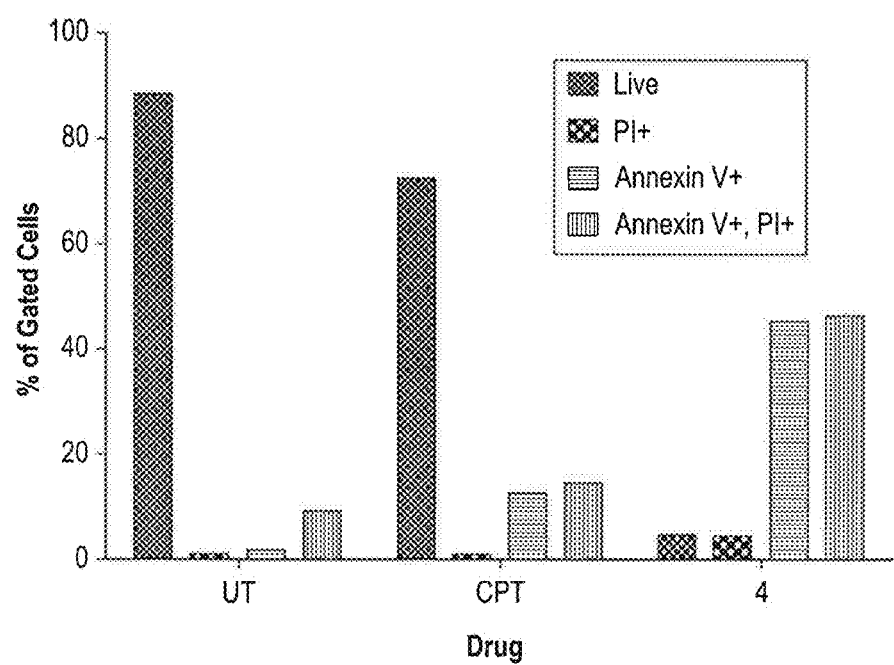
FIG. 6G is a graph showing percentages of cells gated as follows: Live (Viable cells), PI+ (necrosis), AnnexinV+ (late apoptosis), AnnexinV+, PI+ (early apoptosis).
Figure 7A:
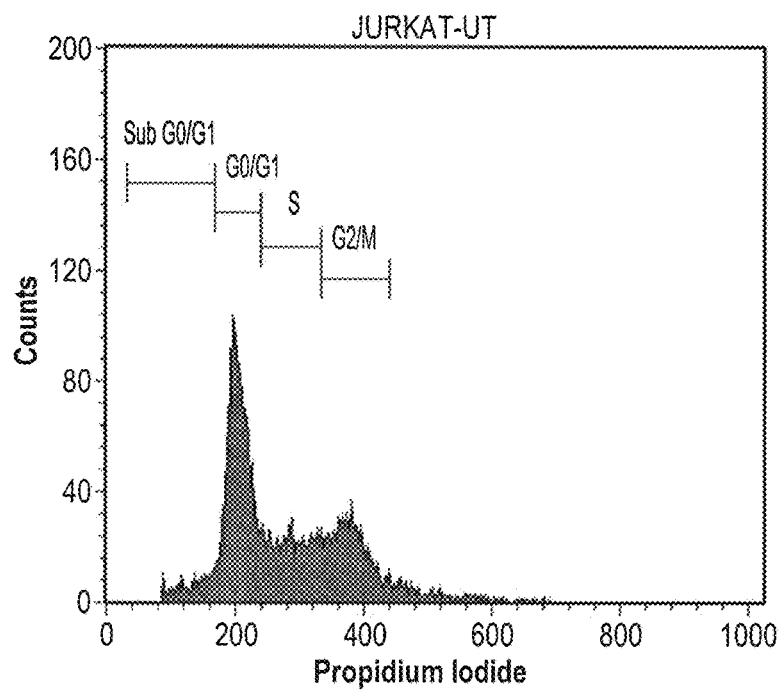
FIGS. 7A-7D are graphs depicting analysis of effects of heterocyclic hybrid compound 4 on the cell cycle distribution of Jurkat cells: propidium iodide staining of untreated Jurkat cells (UT) (FIG. 7A), CPT treated Jurkat cells (CPT; positive control) (FIG. 7B) and compound 4 treated Jurkat cells (FIG. 7C) after 48 h incubation as analyzed by flow cytometry.
Figure 7B:
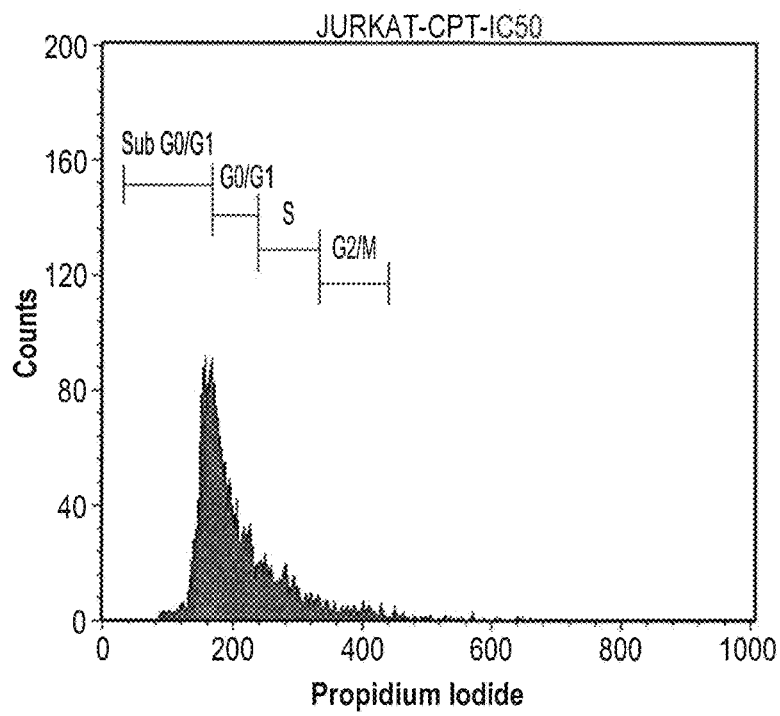
Figure 7C:
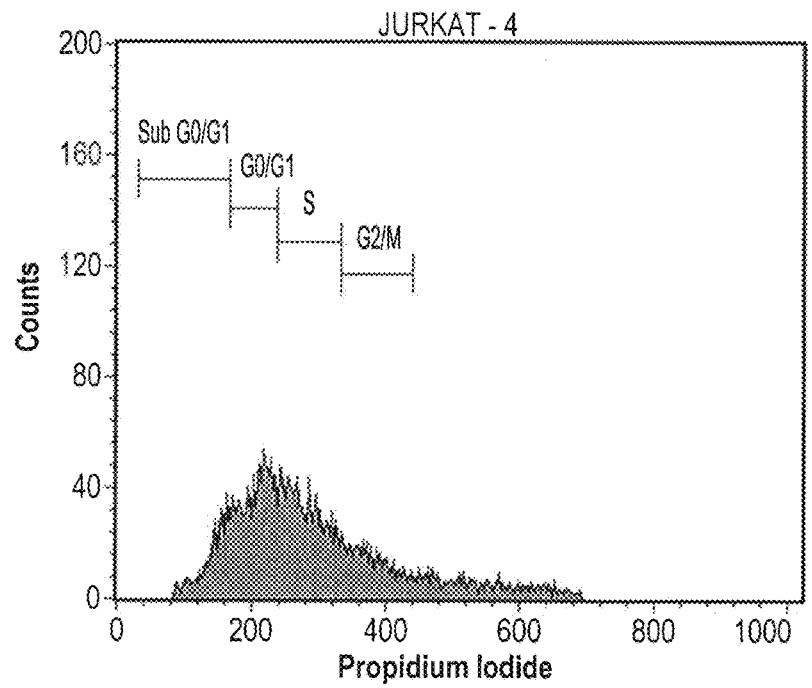
Figure 7D:
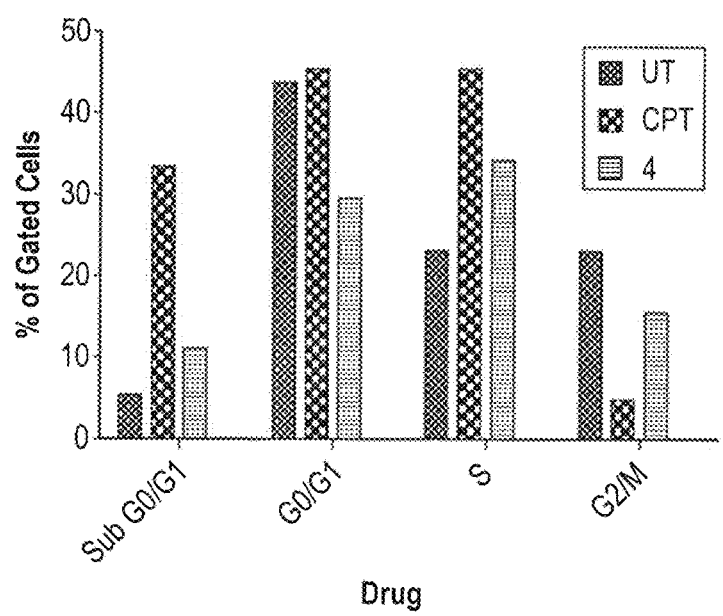

As described in detail herein, a cytotoxicity assay of compound 4 was performed on four human cancer cell lines—JURKAT, NCI-H460, HCT116 and MCF7—with camptothecin (CPT) as a positive control. The inhibitory effects of compound 4 on JURKAT, NCI-H460, HCT116 and MCF7 cancer cells were determined by an MTT (3-[4, 5-dimethylthiazol-2-yl]-2,5 diphenyltetrazolium bromide) assay. The cancer cells were exposed to compound 4 at various concentrations of 1, 5, 10, 15, and 20 μM for different incubation periods of 24 h and 48 h. Proliferation of the cancer cells was significantly inhibited in a concentration-dependent manner for 24 and 48 hours, with the most potent activity being found after 48 h (FIG. 5). When compared to the positive control CPT (40 μM), compound 4 showed a higher inhibition at concentrations of 15 μM and 20 μM. The $IC_{50}$ (half maximal inhibitory concentration) values of compound 4 on the JURKAT cells at 24 h and 48 h was 15.56 μM and 10.33 μM, respectively (FIG. 4).

Apoptosis is a genetically-controlled physiological process, which prevents the proliferation of damaged cells by activating cell death. Programmed cell death can be initiated by several pathways. Previous studies on other anti-cancer drugs, such as cisplatin or paclitaxel, have shown induction of the two different pathways of cell death, necrosis and apoptosis, in different proportions.

To determine whether the antiproliferative effect of compound 4 can trigger cell apoptosis, the percentage of JURKAT cells undergoing apoptosis was determined by flow cytometric analysis after the cells were stained with FITC Annexin V and proidium iodide (PI). The JURKAT cells fell into four different populations, as revealed by the FACScan analysis: healthy cells (FITC Annexin V and proidium iodide negative, "Live"), cells undergoing early apoptosis (FITC Annexin V positive and proidium iodide negative, "AnnexinV$^+$"), cells exhibiting late apoptosis or necrosis (FITC Annexin V and proidium iodide positive, "AnnexinV$^+$, PI$^+$") and a dead cell population (proidium iodide positive, "PI$^+$"). As depicted in FIGS. 6A-6G, after 48 h of treatment with compound 4, a significant accumulation of AnnexinV$^+$ was observed, relative to CTP treated cells. 45.21% and 12.54% of cells were determined to be in early apoptosis (AnnexinV$^+$) when treated with compound 4 and CTP, respectively. Similarly, 46.32% and 14.33% of cells were determined to be in late apoptosis (AnnexinV$^+$, PI$^+$) when treated with compound 4 and CTP, respectively.

Figure 8A:
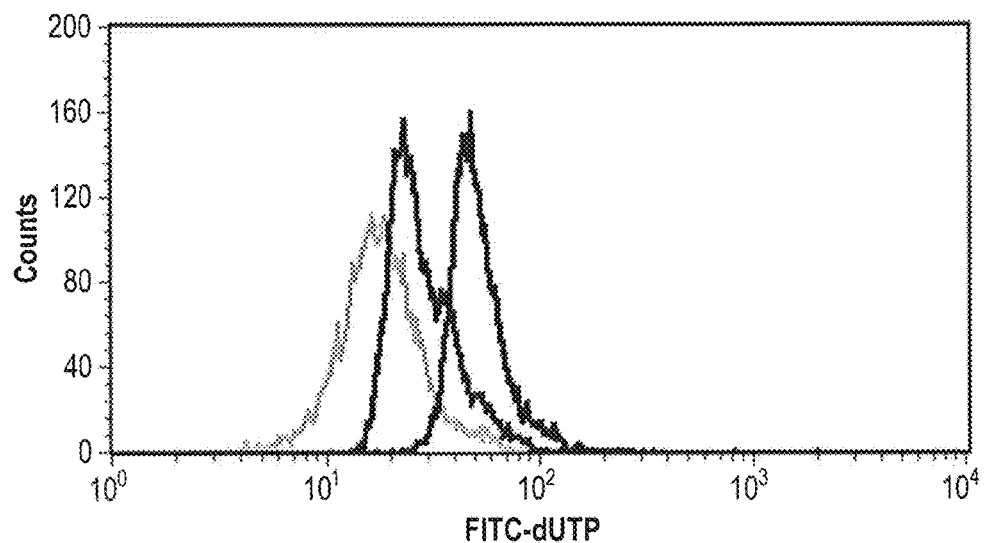
FIG. 8A depicts flow cytometric analysis of DNA fragmentation of untreated Jurkat cells (light grey line), cells treated with compound 4 (black line), and cells treated with CPT (dark grey line) after 48 h of treatment stained for TUNEL assay.
Figure 8B:
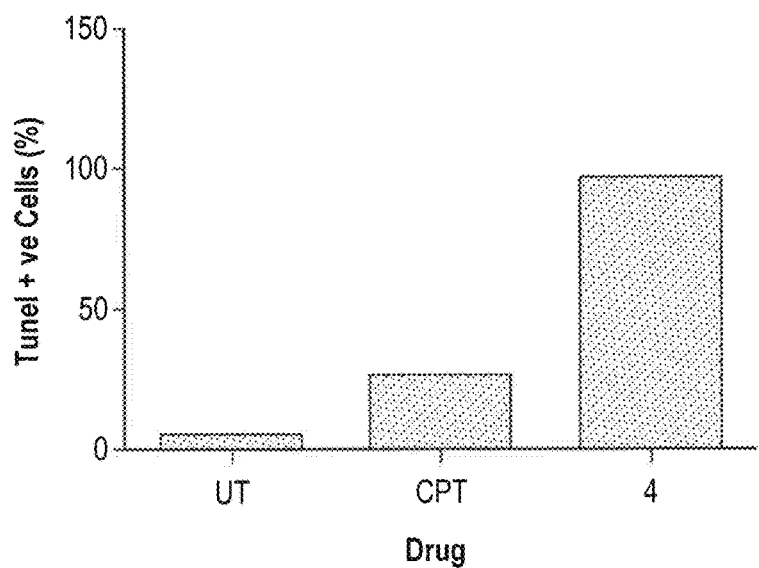
FIG. 8B is a graph depicting percentages of cells gated as TUNEL positive.
Figure 9A:
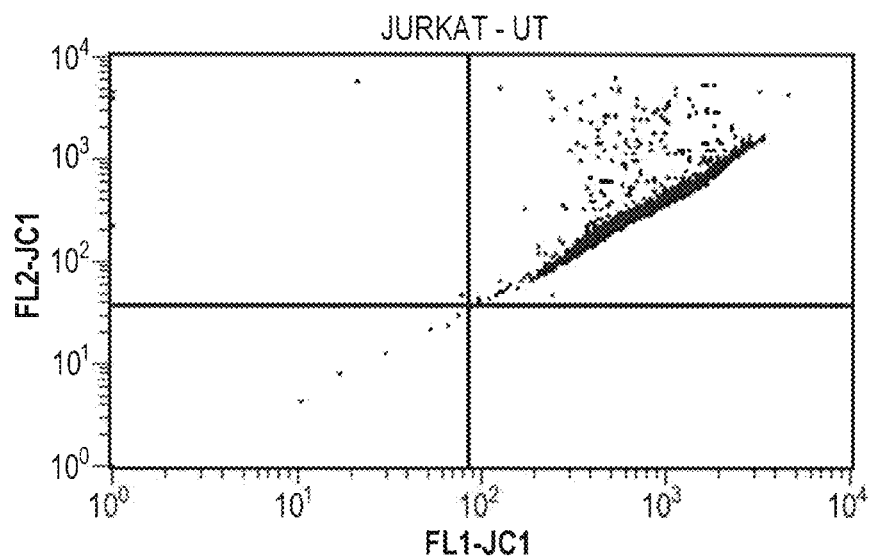
FIGS. 9A-9C depict flow cytometric analysis of loss of mitochondrial membrane potential (MMP or ΔΨm) in JC-1 staining of untreated Jurkat cells (UT) (FIG. 9A), CPT treated Jurkat Cells (CPT; positive control) (FIG. 9B), and compound 4 treated Jurkat cells after 48 h of treatment as analyzed by flow cytometry (FIG. 9C).
Figure 9B:
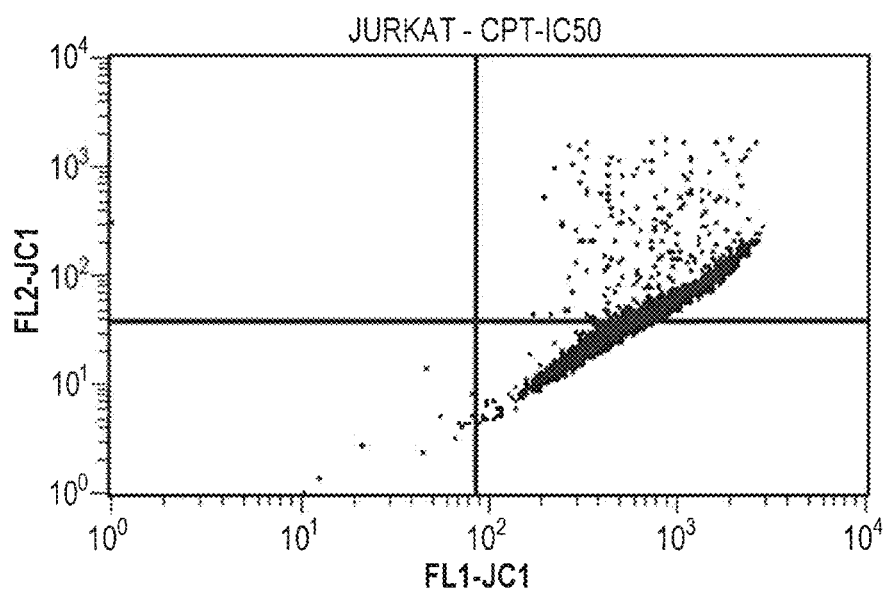
Figure 9C:
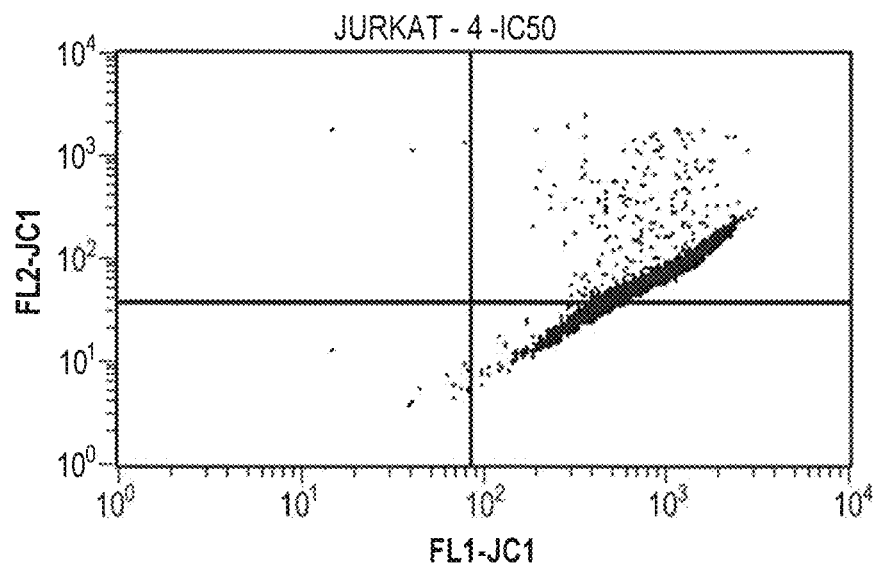
Figure 9D:
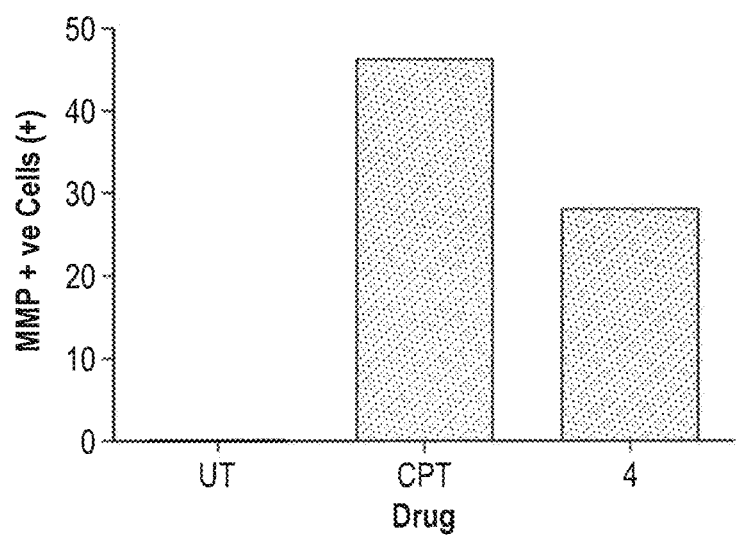
FIG. 9D is a graph depicting percentages of MMP positive cells for each treatment condition.

DNA fragmentation is a key feature of apoptosis, and is largely due to activation of endogenous endonucleases that induce cleavage of chromatin DNA into internucleosomal fragments of roughly 180 base pairs. Apoptosis can be qualitatively assessed by monitoring DNA fragmentation trends, for instance, using terminal deoxynucleotidyl transferase dUTP nick end labeling (TUNEL) assay. For untreated JARKAT cells, TUNEL assay results indicated a constant base line of TUNEL-positive cells. After treatment with compound 4 for 48 h, there was significant increase in the number of TUNEL-positive cells when compared with untreated or control cells. Thus, compound 4-treated JARKAT cells showed increased DNA fragmentation, a hallmark of apoptosis, relative to CTP (control) treated JURKAT cells (FIGS. 8A-8B).

Cancer cells exhibit deregulation of the cell cycle and frequently display cell cycle abnormalities and accumulate mutations, leading to uncontrolled proliferation and genomic instability. Therefore, interruption of cell cycle progression is an important target for cancer treatment. JURKAT cells were treated with compound 4 for 48 h and stained with propidium iodide to determine the proportion of cells undergoing apoptosis or cell death as analyzed by flow cytometry. The percentage of compound 4-treated cells in S phase significantly increased, while those in sub G0/G1 phase moderately increased when compared to untreated cells. The percentage of compound 4-treated cells decreased in G0/G1 and G2/M phase. Similar results were seen in CTP treated cells, which exhibited similar patterns of induction of cell cycle arrest. Thus, these results indicate compound 4 treatment of JURKAT cells creates a significant block of cell cycle at the S and sub G0/G1 phases (FIGS. 7A-7D). Checkpoints are the pathways that halt progression of the cell cycle in response to cellular stress. Targeting checkpoint pathways are potential anti-cancer strategies because abrogation of checkpoint function drives tumor cells toward apoptosis and enhances the efficacy of oncotherapy.

Mitochondrial membrane depolarization is an early event in apoptosis. Chemotherapeutic agents usually induce apoptosis via the mitochondrial pathway. Evaluation of the effect of compound 4 treatment on mitochondrial membrane depolarization was determined using flow cytometry after staining with mitochondrial potential-sensitive dye JC-1. Significant decrease in mitochondrial membrane potential ($\Delta\Psi$m) was observed in compound 4-treated JURKAT cells compared to control (untreated) cells (FIGS. 9A-9D). This result suggests that compound 4 promotes mitochondrial membrane potential disruption in JURKAT cells.

Figure 10A:
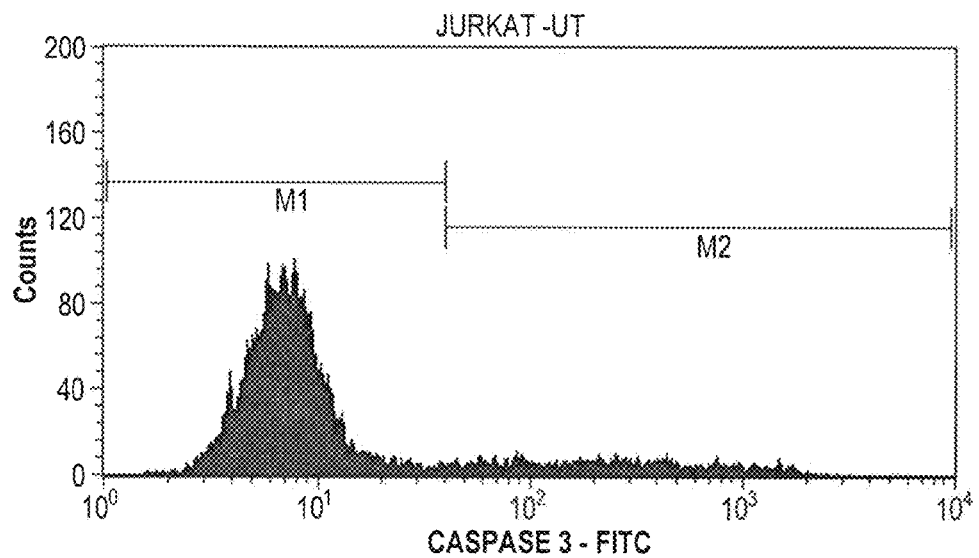
FIGS. 10A-10C depicts flow cytometric analysis of caspase-3 expression in FITC labeled untreated Jurkat cells (UT) (FIG. 10A), in CPT treated Jurkat Cells (CPT; positive control) (FIG. 10B), and in compound 4 treated Jurkat cells (FIG. 10C) after 48 h incubation as analyzed by flow cytometry.
Figure 10B:
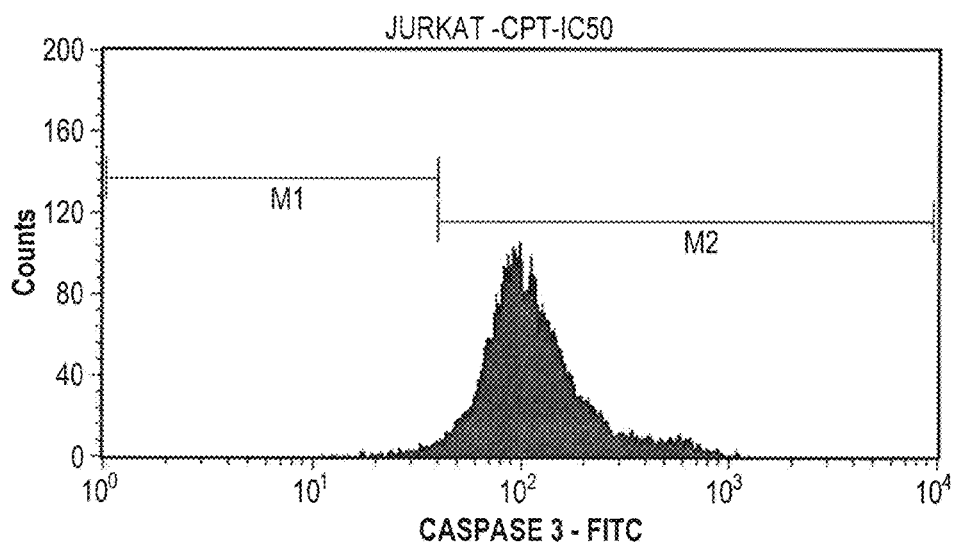
Figure 10C:
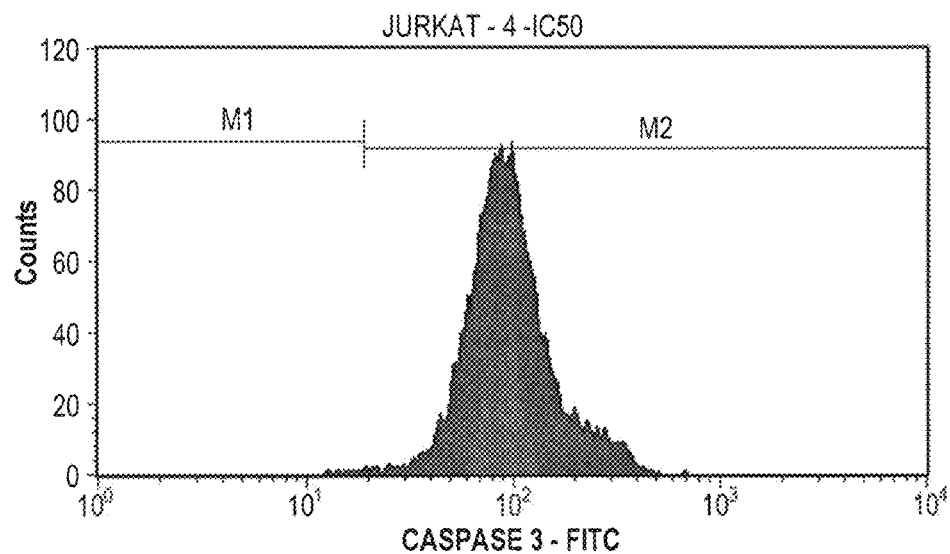
Figure 10D:
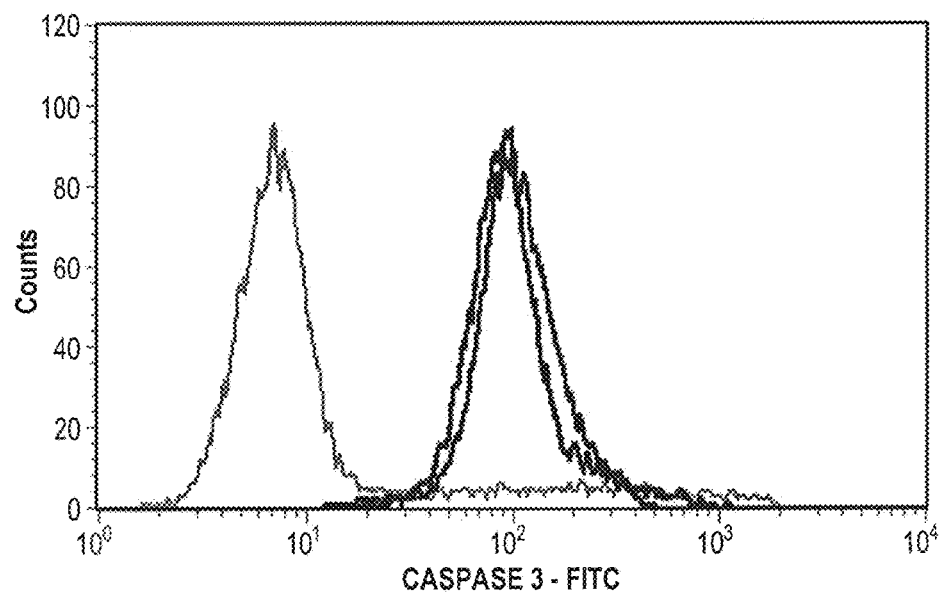
FIG. 10D depicts data analyses of gated cells represented in line chat shows untreated Jurkat cells (light grey line), treated with compound 4 (black line) and CPT (dark grey line).
Figure 10E:
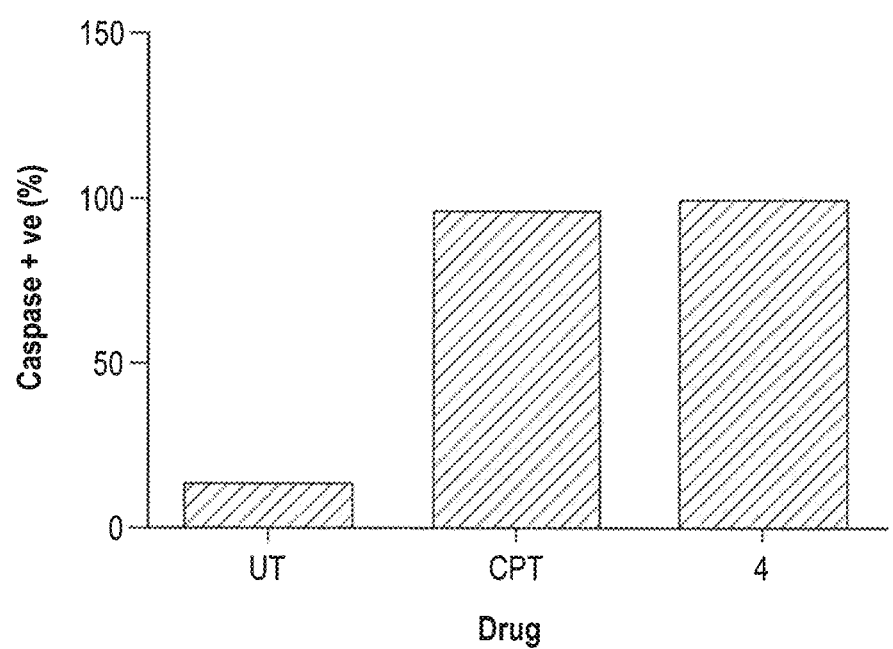
FIG. 10E is a graph depicting percentages of caspase-3 positive gated cells.

Caspase-3 expression was measured using FITC staining. Compound 4-treated JURKAT cells showed higher caspase-3 expression than CPT control treated cells (FIGS. 10A-10-E). Apoptotic caspases are believed to be activated in a protease cascade in which the activated apical caspases responding to apoptotic stimuli directly activate the executioner (effector) caspases in a precisely controlled process. Among these effector caspases, caspase-3, a member of the cysteine protease family, plays a central role in the execution phase of both intrinsic (mitochondrial) and extrinsic (death receptor) pathways of apoptosis by cleaving many key cellular proteins, such as poly (ADP ribose) polymerase (PARP), inhibitor of caspase-activated DNase (ICAD), and several others.

Considered in aggregate with the above summarized results, this increase in caspase-3 expression following treatment with compound 4 is likely due to apoptosis inducement through mitochondrial apoptotic pathways.

Compound 4 can exhibit broad spectrum anti-cancer activity in a dose dependent manner. Results from the assays described herein suggest that compound 4 can be useful for apoptosis induction involving the intrinsic pathway. Compound 4 is thus a promising anti-cancer and chemotherapeutic agent.

The present teachings are illustrated by the following examples.

EXAMPLES

General Synthesis and Characterization Methods

Melting points (mp) are reported uncorrected and were taken using open capillary tubes. $^1$H, $^{13}$C and two-dimensional NMR spectra were recorded on a Bruker 500 MHz instrument in $CDCl_3$ using Tetramethylsilane (TMS) as internal standard. Standard Bruker software was used throughout. Chemical shifts are given in parts per million (δ-scale) and the coupling constants are given in Hertz. IR spectra were recorded on a Perkin Elmer system 2000 FT-IR instrument (KBr). Elemental analyses were performed on a Perkin Elmer 2400 Series II Elemental CHNS analyzer (Waltham, Mass., USA).

Example 1

Experimental Methods and Materials for Synthesis of Compound 4

An equimolar mixture of 3,5-bis[(E)-p-bromophenylmethylidene]tetrahydro-4(1H)-pyridinone 1 (e.g., 0.100 g), acenaphthenequinone 2 (e.g., 0.046 g) and 1,2,3,4-tetrahydroisoquinoline-3-carboxylic acid 3 (e.g., 0.045 g) in 100 mg of [bmim]Br was irradiated in a CEM microwave synthesizer at 100° C. for 9 min. After completion of the reaction, as determined by thin-layer chromatography (TLC), ethyl acetate (10 mL) was added and the reaction mixture was stirred for 15 min. The ethyl acetate layer was then separated and washed with water (50 mL) and the solvent was evaporated under reduced pressure. The resulting precipitate was dried in vacuum and subjected to column chromatography from a petroleum ether-ethyl acetate mixture (6:4) to obtain pure compound 4.

Characterization Data for Exemplary Compound 4:

Obtained as a pale brown solid, (0.155 g, 92%); mp=183-185° C.; IR (KBr): 1599, 1688, 3423 cm$^{-1}$; $^1$H NMR (500 MHz, CDCl$_3$): $\delta_H$ 2.85 (dd, 1H, J=15.0, 13.5 Hz, H-18), 2.99 (d, 1H, J=12.0 Hz, H-25), 3.07 (dd, 1H, J=15.0, 5.0 Hz, H-18), 3.23 (d, 1H, J=13.5 Hz, H-13), 3.34 (d, 1H, J=17.0 Hz, H-24), 3.59 (d, 1H, J=13.5 Hz, H1-13), 3.63 (dd, 1H, J=17.0, 3.0 Hz, 11-24), 4.22-4.26 (m, 2H, H-20 and H-25), 4.40-4.45 (m, 1H, H-19), 6.17 (s, 1H, H-26), 6.27 (d, 2H, J=9.0 Hz, ArH), 6.73 (d, 1H, J=7.5 Hz, ArH), 7.03 (d, 1H, J=7.0 Hz, ArH), 7.11-7.14 (m, 1H, ArH), 7.17 (d, 1H, J=6.5 Hz, ArH), 7.21-7.24 (m, 3H, ArH), 7.35-7.38 (m, 1H, ArH), 7.42 (d, 2H, J=8.5 Hz, ArH), 7.47-7.51 (m, 3H, ArH), 7.58 (d, 1H, J=8.0 Hz, ArH), 7.62 (d, 1H, J=6.5 Hz, ArH), 7.72 (d, 1H, J=8.0 Hz, ArH). $^{13}$C NMR (125 MHz, CDCl$_3$): $\delta_C$ 34.35, 47.93, 51.79, 52.83, 56.31, 62.96, 72.62, 94.41, 121.23, 121.43, 122.80, 124.34, 125.88, 125.97, 126.39, 126.55, 127.43, 127.53, 127.70, 130.66, 130.77, 130.95, 131.07, 131.77, 131.86, 132.00, 132.69, 133.61, 134.37, 135.22, 135.33, 135.70, 136.63, 136.77, 138.40, 196.46. Anal. calcd for $C_{40}H_{30}Br_2N_2O_2$: C, 65.77; H, 4.14; N, 3.83%; found: C, 65.98; H, 4.30; N, 3.71%.

Example 2

Biological Activities of Compound 4

Materials and Methods:

DMEM (Cat no. AL111) Fetal Bovine Serum (Cat no. RM10432) and DPBS (Cat no. TL1006) were purchased from HiMedia (Mumbai, India). Propidium Iodide (cat 556463) APO-DIRECT™ Kit (Cat no. 556381), FITC Rabbit Anti-Active Caspase-3 (Cat no. 560901); FITC Annexin V Apoptosis Detection Kit I (Cat no. 556547); MitoScreen JC-1 Kit (Cat No. 551302) were obtained from BD Biosciences (San Jose, Calif., USA) and camptothecin (Cat No: C9911) was procured from Sigma-Aldrich (St. Louis, Mo., USA).

Stock Preparations

The stock solutions of 1 mM compound 4 and camptothecin (40 µM) were prepared, respectively, in DMSO. Further dilutions of 1, 5, 10, 15, and 20 µM were made in Dulbecco's Modified Eagle's Medium (DMEM) for treatment of cancer cells.

Cell Culture

MCF-7 (human breast cancer); HCT116 (human colon cancer); NCI-H460 (human non-small lung cancer); and JURKAT (human T-cell lymphoma) cell lines were obtained from the National Centre for Cell Science (NCCS, Pune, India). All cells were cultured in DMEM—except JURKAT cells, which were cultured in RPMI media—and supplemented with 10% fetal bovine serum (HiMedia, India) with penicillin (100 I.U/mL) and streptomycin (100 µg/mL) at 37° C. in a humidified atmosphere of 5% $CO_2$ in air. Cultured cells of 75-85% confluency were used for the assays. Adherent cells were trypsinized, counted and seeded in 96-well plates for viability studies. Cells were allowed to adhere overnight before treatment in the experiments. JURKAT cells were washed with D-PBS, counted and seeded in 96-well plates for viability studies.

Cytotoxicity Assay

Cytotoxicity of compound 4 for JURKAT cells was determined by 3-(4,5-dimethylthiazol-2-yl)-2,5-diphenyltetrazolium bromide (MTT) assay. In brief, cells were seeded with different concentrations of compound 4—specifically 1, 5, 10, 15, and 20 µM—in 96 wells plate at a density of 20000 cells per well and incubated for 24 h and 48 h at 37° C., in a $CO_2$ incubator. The MTT assay was performed according to manufacturer instructions and absorbance of the treated and untreated cells were measured in a microplate reader at 570 nm wavelength. Results were represented as percentage of viability={[A570 (treated cells)−background]/[A570 (untreated cells)−background]}× 100. Each treatment was performed in triplicate (N=3).

Apoptosis Assay

Apoptosis assay was performed using FITC Annexin V Apoptosis Detection Kit I (BD Biosciences, San Jose, Calif., USA). The fluorescence intensities of FITC-conjugated Annexin V and PI in compound 4 treated, control treated and untreated cells were analyzed using flow cytometry. Briefly, JURKAT cells (1×10$^6$ cells/well) were seeded in a 6-well plate. After overnight growth, cells were treated with compound 4 (IC$_{50}$ 10.33 µM) for 48 h. Following trypsinization, cells were centrifuged at 1000×g for 10 min, and the pellet was gently resuspended in 100 µL FITC Annexin V binding buffer and then incubated with 5 µL of FITC Annexin V in the dark for 10 min at 25° C. The cells were then centrifuged at 2000 rpm for 5 min, gently resuspended in 500 µL of FITC Annexin V binding buffer and 5 µL of PI was added in an ice bath, followed by flow cytometry (BD FACS Calibur, San Jose, Calif., USA) the apoptotic cells were analyzed using Cell Quest software.

Cell Cycle Analysis

The cell cycle phase evaluation was performed as described by Grassi et al. (2007). Jurkat cells were plated at 1×106 cells/well in a six-well plate for 12 h and then cells were exposed with compound-4 in serum-free media and incubated for an additional 48 h. The $IC_{50}$ (10.33 μM) determined from the cytotoxicity assay for each exposure was used in the cell cycle assay. Following trypsinization, cells were centrifuged at 1000×g for 10 min, and the pellet was resuspended in PBS. Fixation was completed by adding 70% cold ethanol for at least 2 h. The fixed cells were centrifuged at 1000 g for 10 min, and the pellet suspended in PBS. After 60 s, the cells were centrifuged as before, and the pellet resuspended in 1 ml of propidium iodide (PI) staining solution. Immediately after 15 min incubation at 37° C., the cells were analyzed to determine the cell cycle stage using flow cytometry (BD FACS Calibur, San Jose, Calif., USA) with an excitation wavelength of 488 nm and an emission at 670 nm using the Cell Quest software for analysis. The data presented represent at least three independent experiments conducted in triplicate (N=3).

DNA Fragmentation by TUNEL Assay

DNA fragmentation was monitored in treated, control treated and untreated JURKAT cells to identify stages of apoptosis. Briefly, JURKAT cells (1×10$^6$ cells/well) were treated with compound 4 at $IC_{50}$ (10.33 μM), CPT at $IC_{50}$ (40 μM), or untreated for 48 h, and then harvested. Supernatant and adherent cells were collected in a centrifuge tube and then washed twice with PBS. The cells were fixed with 70% ice-cold ethanol by incubating at −20° C. for 30 min. The fixed cells were resuspended in wash buffer, and then washed twice by centrifugation. 50 μl of DNA labeling solution was added to each cell pellet. The cell pellets were incubated with the DNA labeling solution at 37° C. for 60 min. The cell pellets were rinsed with rinse buffer and then resuspended with 0.5 ml of PI/RNase Staining Buffer and incubated for 30 min at RT. Flow cytometry was performed to detect DNA fragmentation (BD FACS Calibur, San Jose, Calif., USA).

Mitochondrial Membrane Potential ($\Delta\Psi_m$) Assay:

Mitochondrial membrane potential ($\Delta\Psi_m$) was determined using JC-1, a fluorescent carbocyanine dye (Smiley et al., 1991). Briefly, JURKAT cells (1×10$^6$ cells/well) were seeded in a 6-well plate. After 48 h of exposure with compound 4 $IC_{50}$ (10.33 μM), CPT $IC_{50}$ (40 μM) or no drug, cells were harvested and then fixed with 70% ice cold ethanol followed by incubation at −20° C. for 30 min. Each of the cell pellets were incubated with 2.5 μM JC-1 for 15 min at 37° C. in darkness. Subsequently, stained cells were washed with PBS, followed by FACS analysis (BD FACS Calibur, San Jose, Calif., USA).

Caspase-3 Expression Assay:

Briefly, JURKAT cells (1×10$^6$ cells/well) were seeded in a 6-well plate. After letting the cells adhere for 12 h, the cells were treated with compound 4 at $IC_{50}$ (10.33 μM), CPT at $IC_{50}$ (40 μM) or untreated for 48 hrs. The JURKAT cells were harvested and then fixed with 70% ice-cold ethanol followed by incubation at −20° C. for 30 min. The fixed JURKAT cells were washed twice with PBS and treated with 20 μl of Caspase-3-FITC (BD Biosciences) and incubated for 60 min at room temperature in dark conditions. Cells were washed with PBS and resuspended in 0.5 ml of PBS, before analysis for Caspase-3 expression using BD FACS Callibur (San Jose, Calif., USA).

It is to be understood that the anti-cancer compound is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. An anti-cancer compound, comprising the following structural formula:

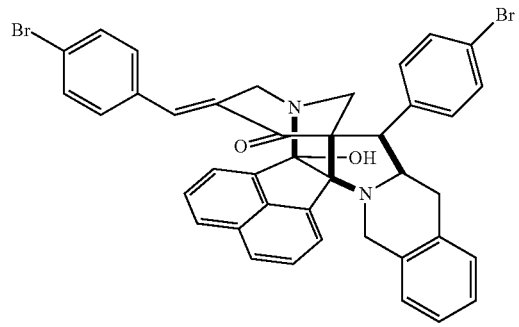

or a pharmaceutically acceptable salt thereof.

2. A pharmaceutical composition comprising the compound according to claim 1, and a pharmaceutically acceptable carrier, diluent or excipient.

3. A method of treating cancer in a patient, comprising administering to said patient a therapeutically effective amount of the compound according to claim 1, wherein the cancer is selected from the group consisting of at least one of blood cancer, breast cancer, colon cancer, and lung cancer.

4. The method of claim 3, wherein the cancer is a blood cancer.

5. A method of making the compound according to claim 1, comprising the steps of:
   mixing 3,5-bis[(E)-p-bromophenylmethylidene]tetrahydro-4(1H)-pyridinone, acenaphthenequinone, 1,2,3,4-tetrahydroisoquinoline-3-carboxylic acid and 1-butyl-3-methylimidazolium bromide ([Bmim]Br) to form a mixture;
   irradiating the mixture with microwaves; and
   cooling the mixture after irradiating to form a precipitate.

6. The method of claim 5, wherein the mixture comprises equimolar amounts of the 3,5-bis[(E)-p-bromophenylmethylidene]tetrahydro-4(1H)-pyridinone, acenaphthenequinone and 1,2,3,4-tetrahydroisoquinoline-3-carboxylic acid.

7. The method of claim 5, further comprising the steps of:
   washing the precipitate in ethyl acetate; and
   drying the precipitate.

8. The method of claim 7, further comprising the steps of:
   subjecting the dried precipitate to column chromatography from a petroleum ether-ethyl acetate mixture.

* * * * *

UNITED STATES PATENT AND TRADEMARK OFFICE
CERTIFICATE OF CORRECTION

PATENT NO. : 10,357,485 B1
APPLICATION NO. : 16/143875
DATED : July 23, 2019
INVENTOR(S) : Abdulrahim Ibrahim Almansour et al.

Page 1 of 1

It is certified that error appears in the above-identified patent and that said Letters Patent is hereby corrected as shown below:

On the Title Page

Item (72) two inventors' addresses should be corrected to:
Kotresha Dupadahalli, Karnataka (IN)
Jose Carlos Menendez, Madrid (ES)

Signed and Sealed this
Nineteenth Day of November, 2019

Andrei Iancu
*Director of the United States Patent and Trademark Office*